(12) United States Patent
Nesbitt

(10) Patent No.: US 9,913,595 B2
(45) Date of Patent: *Mar. 13, 2018

(54) ANTI-MICROBIAL ELECTROMYOGRAPHY NEEDLE

(71) Applicant: Innovatech, LLC, Chicago, IL (US)

(72) Inventor: Bruce Nesbitt, Chicago, IL (US)

(73) Assignee: Innovatech, LLC, Chicago, IL (US)

( * ) Notice: Subject to any disclaimer, the term of this patent is extended or adjusted under 35 U.S.C. 154(b) by 98 days.

This patent is subject to a terminal disclaimer.

(21) Appl. No.: 15/138,791

(22) Filed: Apr. 26, 2016

(65) Prior Publication Data

US 2016/0235327 A1  Aug. 18, 2016

Related U.S. Application Data

(63) Continuation of application No. 13/907,226, filed on May 31, 2013, now Pat. No. 9,332,921.

(51) Int. Cl.
| | |
|---|---|
| *A61B 5/0492* | (2006.01) |
| *A61B 5/00* | (2006.01) |
| *A01N 59/16* | (2006.01) |
| *A01N 59/20* | (2006.01) |
| *A61L 31/10* | (2006.01) |
| *A61L 31/16* | (2006.01) |

(52) U.S. Cl.
CPC ............ *A61B 5/0492* (2013.01); *A01N 59/16* (2013.01); *A01N 59/20* (2013.01); *A61B 5/685* (2013.01); *A61B 5/6848* (2013.01); *A61L 31/10* (2013.01); *A61L 31/16* (2013.01); *A61L 2300/404* (2013.01); *A61L 2420/06* (2013.01)

(58) Field of Classification Search
CPC ... A61B 5/0492; A61B 5/6848; A61B 5/6849; A61B 5/685
See application file for complete search history.

(56) References Cited

U.S. PATENT DOCUMENTS

| | | | |
|---|---|---|---|
| 6,238,686 | B1 | 5/2001 | Burrell et al. |
| 6,716,895 | B1 | 4/2004 | Terry |
| 7,147,634 | B2 | 12/2006 | Nesbitt |
| 7,283,866 | B2 | 10/2007 | Mumford et al. |
| 7,838,082 | B2 | 11/2010 | Nesbitt |
| 7,955,637 | B2 | 6/2011 | Nesbitt |
| 8,048,471 | B2 | 11/2011 | Nesbitt |
| 8,231,926 | B2 | 7/2012 | Nesbitt et al. |
| 8,231,927 | B2 | 7/2012 | Nesbitt et al. |
| 8,374,669 | B2 | 2/2013 | Espenhain |
| 8,409,656 | B2 | 4/2013 | Bay et al. |
| 9,332,921 | B2 * | 5/2016 | Nesbitt |

(Continued)

FOREIGN PATENT DOCUMENTS

WO    WO 2013/134421    9/2013

OTHER PUBLICATIONS

"Concentric and Monopolar electromyographic (EMG) needles" written by Nazarena Mazzaro, published in May 2007.

(Continued)

*Primary Examiner* — Lee S Cohen
(74) *Attorney, Agent, or Firm* — Neal, Gerber & Eisenberg LLP

(57) ABSTRACT

A coated electromyography needle including an anti-microbial, electrically insulative coating applied to non-tip portion of an electrode of the electromyography needle.

37 Claims, 1 Drawing Sheet

(56) References Cited

U.S. PATENT DOCUMENTS

| | | |
|---|---|---|
| 2006/0259033 A1 | 11/2006 | Nesbitt |
| 2007/0225610 A1 | 9/2007 | Mickley et al. |
| 2007/0299409 A1 | 12/2007 | Whitbourne et al. |
| 2010/0285084 A1 | 11/2010 | Yang et al. |
| 2011/0021899 A1 | 1/2011 | Arps et al. |
| 2011/0071379 A1 | 3/2011 | Rea et al. |
| 2011/0182960 A1 | 7/2011 | Van Dongen et al. |

OTHER PUBLICATIONS

G. A. West, C. D. Watson, Gamma Radiation Damage and Decontamination Evaluation of Protective Coatings and Other Materials for Hot Laboratory and Fuel Processing Facilities, published in Feb. 1965 for Oak Ridge National Laboratory operated by Union Carbide Corporation for the U.S. Atomic Energy Commission (45 pages).

* cited by examiner

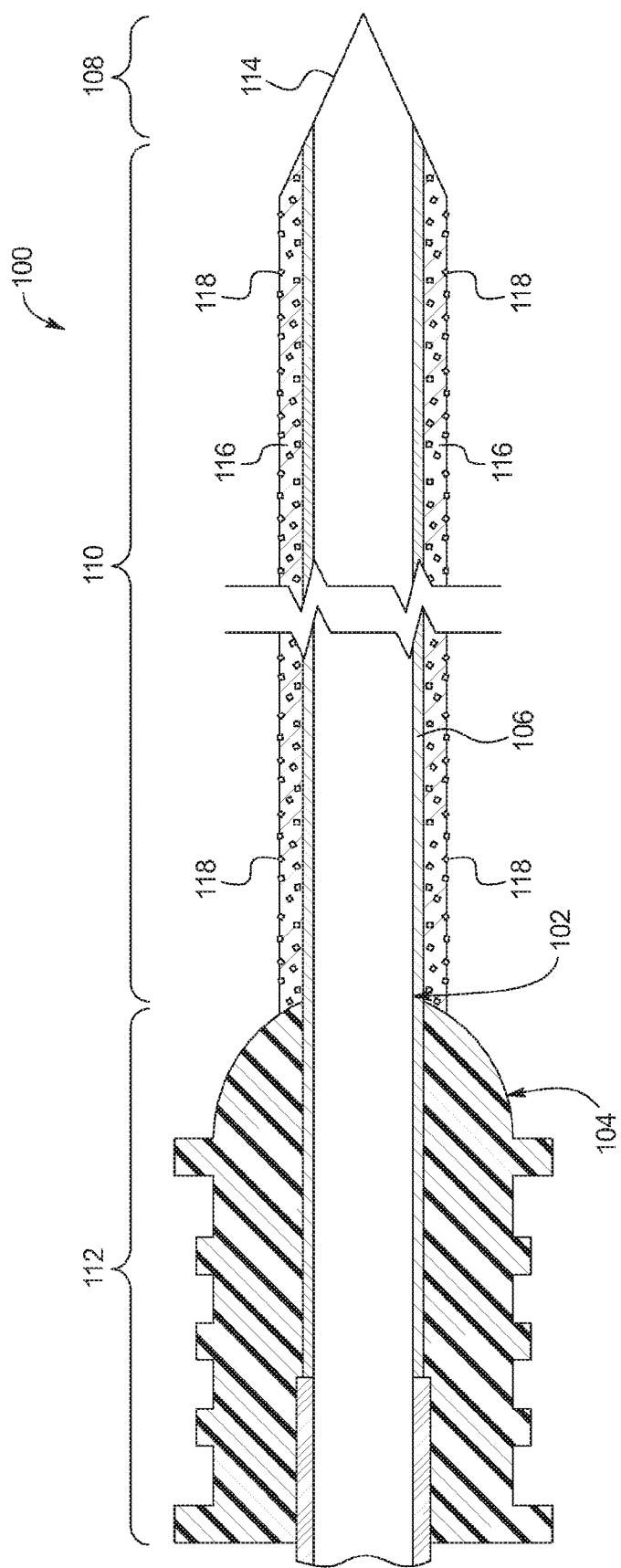

ANTI-MICROBIAL ELECTROMYOGRAPHY NEEDLE

PRIORITY CLAIM

This application is a continuation of, claims priority to, and the benefit of U.S. patent application Ser. No. 13/907,226, filed May 31, 2013, now U.S. Pat. No. 9,332,921 issued May 10, 2016, the entire contents of which is incorporated herein by reference.

BACKGROUND

Muscular movement involves nerves controlling muscles with electrical signals called impulses. Electromyography ("EMG") involves the testing of the electrical activity of muscles at rest and when contracted. EMG specifically measures muscle response or electrical activity in response to a nerve's simulation of the muscle.

An EMG needle is used to perform an intramuscular EMG procedure. An EMG needle includes a cylindrical electrode having an elongated body. The elongated body of the electrode includes a distal end or tip portion (which defines a pointed or sharpened tip), a middle unsharpened, non-tip portion and an unsharpened proximal end or handle connecting portion. The EMG needle includes a handle, such as a molded plastic handle or hub, connected at or to the proximal end or handle connecting portion of the elongated body of the electrode (i.e., opposite the distal end or tip portion of the elongated body of the electrode). The electrode is electrically connected to an electric signal measuring and recording instrument, such as an electromyograph, to measure, record and display the electrical activity of the muscle tissue.

The EMG needle is typically either a monopolar EMG needle or a concentric EMG needle. A monopolar EMG needle is made of metal, such as stainless steel, wherein the whole needle, except for the tip or distal end, is coated with an electrically insulating material, such as polytetrafluoroethylene (PTFE). The tip is sharpened to a conical shape and functions as the conductive receptor area (i.e., the electrical activity reception area) of the monopolar EMG needle. A concentric EMG needle includes a cannula and a core (made of different metals), wherein the tip of the concentric EMG needle has a flat elliptical shape. The core is embedded in an electrically insulating material such that the two metal parts of the concentric EMG needle are electrically insulated.

To perform an intramuscular EMG procedure, a medical professional cleans the skin over the area being tested. Following this cleaning, the medical professional inserts part of the electrode of the EMG needle (and specifically at least the sharpened tip portion of the electrode) through the skin and into the muscle tissue. Once inserted into the muscle tissue, the EMG needle (in conjunction with the electric signal measuring and recording instrument) detects the electrical current generated by the muscle cells when the muscle cells are at rest, when the muscle cells are slightly contracted and when the muscle cells are fully or forcefully contracted. This process is repeated several times for different areas of a muscle or for different muscles.

By analyzing the detected electrical current generated by the muscle cells at rest and during different levels of contraction, the medical professional can determine any irregularities in the patient's muscle activity. For example, by analyzing the detected electrical current generated by muscle cells, a medical professional may diagnose diseases that damage muscle tissue, nerves or where nerve and muscle join and/or determine the cause of weakness, paralysis, involuntary muscle twitching or other symptoms.

One potential issue associated with EMG needles is the sterilization or cleanliness of the electrode as the electrode contacts tissue and other parts of the body. Any tissue buildup on the electrode creates an environment where bacteria, biopathogens and other harmful organisms may cultivate and be introduced into the body during the EMG procedure. Furthermore, any gaps between the electrode and the handle/hub enables bacteria, biopathogens and other harmful organisms to get underneath the handle. This further promotes the growth of the bacteria, biopathogens and other harmful organisms which may migrate to the surface of the electrode or to the patient.

Additionally, if the sterilization of the EMG needle is not performed properly, not performed routinely, is consistently interrupted and resumed or not performed at all, bacteria, biopathogens and other harmful organisms can adhere to and grow on the surface of the electrode and then enter a patient's body during the EMG procedure. Moreover, if an EMG needle is reused on the same patient (or used on a different patient), bacteria, biopathogens and other harmful organisms can adhere to and grow on the surface of the electrode and then enter the patient's body when the EMG needle is reused during another EMG procedure. Such entering of bacteria, biopathogens and other harmful organisms into a patient's body can cause significant difficulties and complications for the patient after the EMG procedure is complete. As a result, minimizing the growth of bacteria, biopathogens and other harmful organisms on the surface of the electrode of the EMG needle is needed.

SUMMARY

The present disclosure relates in general to EMG needles having an anti-microbial coating.

In one embodiment, the present disclosure is directed to an EMG needle, such as a monopolar EMG needle or a concentric EMG needle, wherein at least part of a non-tip portion of an elongated body of an electrode of the EMG needle is coated with one or more electrically-insulated, low-friction, anti-microbial coatings. In one embodiment, the EMG needle has an electrode including an elongated body made of a conductive substrate or conductive material. The elongated body includes a sharpened distal end or sharpened tip portion, a middle or non-tip portion adjacent to the tip portion and a proximal end or handle/hub connecting portion adjacent to the non-tip portion. The EMG needle includes a handle or hub connected to the proximal or handle connecting portion of the elongated body of the electrode. One or more wires or other electrical conductors are attached to the proximal end or handle/hub connection portion of the electrode (i.e., opposite the tip portion) to transfer electricity from the electrode to an electric signal measuring device, such as oscilloscope or an electromyograph.

In one embodiment, at least part of the non-tip portion of the elongated body of the electrode is coated with an electrically insulative, anti-bacterial or anti-microbial coating. In this embodiment, the tip portion of the elongated body of the electrode is not coated with the electrically insulative, anti-bacterial or anti-microbial coating. Such an embodiment provides that the uncoated, sharpened tip portion of the elongated body of the electrode enables electrical signals to be detected by the uncoated tip portion of the electrode and then pass thru the electrode and one or more wires to the electric signal measuring device to measure the electrical activity of muscle tissue.

Such an embodiment further prevents or inhibits the growth of bacteria, biopathogens and/or other harmful organisms on surface of the coated, non-tip portion of the electrode of the EMG needle. That is, the coated non-tip portion of the electrode of the EMG needle disclosed herein tends to kill bacteria, biopathogens and/or other harmful organisms that contact the surface of the non-tip portion of the elongated body of the electrode of the EMG needle during and after the EMG procedure. Additionally, the EMG needle disclosed herein can be used multiple times, if necessary, in different EMG procedures without requiring sterilization (even though sterilization is preferred) because the anti-microbial particles tend to kill the bacteria, biopathogens and/or other harmful organisms which contact part of the electrically insulative, low-friction, anti-microbial coating on the surface of the electrode of the EMG needle. The EMG needle disclosed herein therefore adds an element of safety by minimizing the chance of infections or other complications in the body after the EMG procedure is complete.

Additional features and advantages are described herein, and will be apparent from, the following Detailed Description and the FIGURES.

BRIEF DESCRIPTION OF THE FIGURES

FIG. 1 is a side-cross-sectional view of one embodiment of a coated electromyography needle disclosed herein.

DETAILED DESCRIPTION

As seen in FIG. 1 various embodiments of the present disclosure relate to a partially anti-microbial coated electromyography ("EMG") needle 100. In this embodiment, the EMG needle includes a cylindrical electrode 102 and a holding device, such as handle or hub 104 or other suitable holding device which is connected to the electrode 102 and enables the electrode to be manipulated in an EMG procedure.

The electrode includes a conductive substrate or conductive material which enables the electrode to conduct electrical energy or electricity. The electrode is constructed from any suitable material, including but not limited to metals such as steel (both high- and low-carbon content), stainless steel, titanium, nitinol, and other metals and metal alloys.

The electrode 102 includes an elongated body 106 having a distal or tip portion 108 which forms a sharpened tip 114. The elongated body of the electrode includes a middle or non-tip portion 110 adjacent to the tip portion. The elongated body of the electrode includes a proximal or handle/hub connecting portion 112 adjacent to the middle non-tip portion. It should be appreciated that any suitable dimensions of the tip portion, non-tip portion and handle/hub connecting portion may be implemented in accordance with the present disclosure. For example, the length of the electrode of the EMG needle is 0.98 inches (25 mm) wherein the length of the tip portion is 0.025 inches (0.635 mm) and the length of the remaining electrode is 0.96 inches (24.365 mm).

In one embodiment, the non-tip portion of the surface of the elongated body of the electrode is coated with an electrically insulative coating 116 including a plurality of anti-microbial particles 118. In another embodiment, the non-tip portion and the handle/hub connecting portion of the surface of the elongated body of the electrode are coated with an electrically insulative coating including a plurality of anti-microbial particles. In these embodiments, the tip portion of the surface of the elongated body of the electrode is not coated with the electrically insulative coating including the plurality of anti-microbial particles.

In different embodiments, the electrical insulative coating includes a binder or base material, such as an epoxy, phenolic, phenoxy, polyimide, polyamide, polyamideamide, polyphenylene sulfide, polyarylsulfone, polyethylene, polytetrafluoroethylene, fluorinated ethylene propylene, perfluoroalkoxy, polyetheretherketone (PEEK), polyetherketone (PEK), polyphenlyene sulfide (PPS) or any suitable binder or resin. Such suitable binders or base materials include any binder which, when cured, adheres to the surface of the EMG needle, is electrically insulative, has low-friction properties, is chemically stable, is thermally stable, is resistant to chemicals, and/or is readily sterilized and resistant to contamination. In one such embodiment, the binder or base material is gamma radiation resistant. In one such embodiment, the coating includes an ultraviolet light cure resin to semi cure or fully cure the coating. In another embodiment, the coating includes an electron beam cure resin.

In one embodiment, the coating includes a plurality of interspersed anti-microbial particles. The anti-microbial particles include at least one of the following materials: silver particles, nano-silver particles, silver-oxide particles, ceramic particles, silver ceramic particles, glass silver particles, silver compounds, copper particles, nano-copper particles, cellular copper particles, copper ceramic particles, copper alloy particles (such as brass particles, bronze particles, cupronickel particles, and copper-nickel-zinc particles), copper glass particles, copper compounds, combinations of silver and ceramic particles, combinations of copper and silver particles, combinations of silver, copper and ceramic particles or any other suitable anti-microbial particles and/or anti-bacterial particles or materials. In this embodiment, such anti-microbial particles reduce and tend to kill bacteria, biopathogens and/or other harmful organisms/germs that are located on the coated surface of the electrode or otherwise incorporated into the coating formulation. The anti-microbial particles are capable of killing bacteria, biopathogens and/or other harmful organisms which contact the surface of the coated electrode while in storage, while the electrode is deployed into the body and/or between insertions and manipulations of the electrode into and out of the body (such as any bacteria, biopathogens and/or other harmful organisms located on the patient's skin that are transferred to the coated electrode during the EMG procedure). The coated electrode of the EMG needle therefore minimizes or reduces the chance of infections or other complications in the body after the EMG procedure is complete.

In one embodiment, the coating includes a non-stick material. The non-stick material includes at least one of the following materials: silicone, polytetrafluoralethylene, fluoropolymers, a combination of fluorosilicones and ceramic materials, such as Sol Gel coating materials, with or without silicone additives. It should be appreciated that any suitable non-stick material may be used in the coating. In this embodiment, the non-stick material further minimizes the buildup of tissue on the surface of the electrode by minimizing the adherence of the tissue on the surface of the electrode. Specifically, the non-stick material or coating forms a low-friction slick or slippery surface where a substantial portion of the skin tissue and/or muscle tissue slides or moves off of the electrode.

It should be appreciated that the electrically insulative coating aids the transfer of the detected electrical impulses from the tip portion of the elongated body of the electrode to at least the non-tip portion of the elongated body of the electrode (i.e., the insulative coating prevents the passage of electricity from the conductive substrate of the electrode through the coating). Additionally, the anti-microbial particles of the coating tend kill a substantial amount of the bacteria, biopathogens and/or other harmful organisms that reside on the surface of the non-tip portion of the electrode and any bacteria, biopathogens and/or other harmful organisms that might get through any gap between the handle/hub and the electrode.

In operation, at least part of the tip portion of the elongated body enters muscle tissue of a patient's body during an EMG procedure. Following a medical professional placing at least the tip portion of the elongated body into the designated muscle tissue, electrical energy, such as electricity, is transferred from the muscle tissue to the tip portion of the elongated body of the electrode. The electrical energy is then transferred along the length of the elongated body of the electrode from the tip portion to the non-tip portion and then to the handle/hub connecting portion. The electrical energy is then transferred from the handle/hub connection portion of the electrode of the EMG needle to one or more wires or electrical conductors (not shown) connected to the handle or hub of the EMG needle (and in electrical contact with the handle/hub connection portion of the electrode of the EMG needle). The electrical energy is then transferred through the wiring to an electric signal measuring device (not shown), such as an electromyograph or oscilloscope, which measures, displays and records the amount of electrical energy in the muscle tissue.

In another embodiment, the coating includes additives, such as silane coupling agents, other materials formulated to improve the bonding capabilities of a coating to the surface of the electrode, particularly smooth surfaces, or other materials which modify the curing characteristics or the drying characteristics of the coating before curing. In another embodiment, the coating includes additives to improve the wear characteristics, corrosion resistance, and/or electrical properties of the coating.

In one embodiment, a top coating is applied to the surface of the electrode to coat or cover the anti-microbial particle layer. In different embodiments, the top coating is a low-friction or release coating or material, such as fluorinated materials, polytetrafluoroethylene, perfluoro-alkoxy, fluoro-ethylenepropylene, MFA, polyethylene, silicone, a resin like clear medical grade epoxy in liquid or power form, ceramic composites, paralyene silane polymers, Sol Gel coatings and other suitable low-friction coatings. In this embodiment, part of the top coating is removed (by buffing, sanding or using any other suitable material sanding method) to expose some or all of the anti-microbial particles of the non-tip portion of the surface of the electrode. Accordingly, some or all of the anti-microbial particles protrude from the top coating.

In another embodiment, the handle/hub of the EMG needle includes anti-microbial properties. In one such embodiment, the anti-microbial coating described herein is also applied to the surface of the handle/hub of the EMG needle. In another such embodiment, the handle/hub is formed from any suitable material, such as any suitable plastic, which includes a plurality of anti-microbial particles that tend kill a substantial amount of the bacteria, biopathogens and/or other harmful organisms that reside on the surface of the handle/hub.

It should be appreciated that any suitable manner of applying and curing the electrically insulative coating and the plurality of anti-microbial particles to the non-tip portion of the surface of the electrode of the EMG needle may be implemented. It should be further appreciated that any suitable manner of applying and curing the electrically insulative coating and the plurality of anti-microbial particles to the non-tip portion and the handle/hub connecting portion (to provide antimicrobial protection to any gaps or space between the needle and the hub or handle) of the surface of the electrode of the EMG needle may be implemented. In one example embodiment, the anti-microbial particles are interspersed with the coating and the coating is applied to at least the non-tip portion (and possibly part or all of the handle/hub connecting portion) of the surface of the electrode. In another example embodiment, the electrically insulative coating is first applied to at least the non-tip portion (and possibly part or all of the handle/hub connecting portion) of the surface of the electrode and then the anti-microbial particles are applied to the applied electrically insulative coating.

It should be further appreciated that any suitable manner of not applying the electrically insulative coating and the plurality of anti-microbial particles to the tip portion of the surface of the electrode of the EMG needle may be implemented. In one example embodiment, the tip portion of the electrode is suitably masked, blocked or shielded during the application of the coating to the non-tip portion of the electrode. Such blocking, protecting, shielding or otherwise suitably masking of one or more parts of the electrode provide that at least the non-tip portion of the electrode is coated and the tip portion of the electrode is not coated. In another example embodiment, the tip portion of the electrode is coated and then the applied coated is subsequently removed. Such removal of the applied coating of the tip portion of the electrode provide that at least the non-tip portion of the electrode is coated and the tip portion of the electrode is not coated.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. An electromyography needle comprising:
   an electrode including an elongated body having a sharpened tip portion and a non-tip portion; and
   an electrically insulative coating on a surface of the non-tip portion of said electrode, wherein the electrically insulative coating includes a base material including an epoxy and a fluoropolymer.

2. The electromyography needle of claim 1, wherein the base material includes anti-microbial particles selected from the group consisting of: silver particles, silver-oxide particles, glass-silver particles, a combination of silver and ceramic particles, copper particles, glass-copper particles, a combination of copper and ceramic particles, a combination of copper and silver particles, and a combination of copper, silver and ceramic particles.

3. The electromyography needle of claim 2, which includes a top coating including a plurality of particles of a low-friction material.

4. The electromyography needle of claim 3, wherein a plurality of the anti-microbial particles partially protrude through the top coating.

5. The electromyography needle of claim 1, wherein the electrode is cylindrical.

6. The electromyography needle of claim 1, wherein the electrically insulative coating includes an additive that improves the bonding capabilities of the electrically insulative coating.

7. The electromyography needle of claim 1, wherein the sharpened tip portion has no coating.

8. An electromyography needle comprising:
a handle;
an electrode including an elongated body having a sharpened tip portion, a non-tip portion and a handle connecting portion connected to the handle; and
an electrically insulative coating on a surface of the non-tip portion of said electrode, wherein the electrically insulative coating includes a base material including an epoxy and a fluoropolymer.

9. The electromyography needle of claim 8, wherein the base material includes anti-microbial particles selected from the group consisting of: silver particles, silver-oxide particles, glass-silver particles, a combination of silver and ceramic particles, copper particles, glass-copper particles, a combination of copper and ceramic particles, a combination of copper and silver particles, and a combination of copper, silver and ceramic particles.

10. The electromyography needle of claim 9, which includes a top coating including a plurality of particles of a low-friction material.

11. The electromyography needle of claim 10, wherein a plurality of the anti-microbial particles partially protrude from the electrically insulative coating through the top coating.

12. The electromyography needle of claim 8, wherein the electrically insulative coating is also on a surface of the handle connecting portion of the electrode.

13. The electromyography needle of claim 8, wherein the electrode is cylindrical.

14. The electromyography needle of claim 8, wherein the handle includes a coating having a plurality of anti-microbial particles.

15. The electromyography needle of claim 8, wherein the electrically insulative coating includes an additive that improves the bonding capabilities of the electrically insulative coating.

16. The electromyography needle of claim 8, wherein the sharpened tip portion has no coating.

17. An electromyography needle comprising:
an electrode including an elongated body having a sharpened tip portion and a non-tip portion; and
an electrically insulative coating on a surface of the non-tip portion of said electrode, wherein the electrically insulative coating includes a gamma radiation resistant base material including an epoxy and a fluoropolymer.

18. The electromyography needle of claim 17, wherein the electrically insulative coating includes anti-microbial particles selected from the group consisting of: silver particles, silver-oxide particles, glass-silver particles, a combination of silver and ceramic particles, copper particles, glass-copper particles, a combination of copper and ceramic particles, a combination of copper and silver particles, and a combination of copper, silver and ceramic particles.

19. The electromyography needle of claim 18, which includes a top coating including a plurality of particles of a low-friction material.

20. The electromyography needle of claim 19, wherein a plurality of the anti-microbial particles partially protrude through the top coating.

21. The electromyography needle of claim 17, wherein the sharpened tip portion has no coating.

22. An electromyography needle comprising:
a handle;
an electrode including an elongated body having a sharpened tip portion, a non-tip portion and a handle connecting portion connected to the handle; and
an electrically insulative coating on a surface of the non-tip portion of said electrode, wherein the electrically insulative coating includes a gamma radiation resistant base material including an epoxy and a fluoropolymer.

23. The electromyography needle of claim 22, wherein the electrically insulative coating includes anti-microbial particles selected from the group consisting of: silver particles, silver-oxide particles, glass-silver particles, a combination of silver and ceramic particles, copper particles, glass-copper particles, a combination of copper and ceramic particles, a combination of copper and silver particles, and a combination of copper, silver and ceramic particles.

24. The electromyography needle of claim 23, which includes a top coating including a plurality of particles of a low-friction material.

25. The electromyography needle of claim 24, wherein a plurality of the anti-microbial particles partially protrude through the top coating.

26. The electromyography needle of claim 22, wherein the handle includes a coating having a plurality of anti-microbial particles.

27. The electromyography needle of claim 22, wherein the electrically insulative coating is on a surface of the handle connecting portion of the electrode.

28. The electromyography needle of claim 22, wherein the sharpened tip portion has no coating.

29. An electromyography needle comprising:
an electrode including an elongated body having a sharpened tip portion and a non-tip portion;
an electrically insulative coating on a surface of the non-tip portion of said electrode, wherein the electrically insulative coating includes a binder material, a non-stick material, and an additive; and
a top coating that at least partially covers the electrically insulative coating.

30. The electromyography needle of claim 29, wherein the electrically insulative coating includes anti-microbial particles selected from the group consisting of: silver particles, silver-oxide particles, glass-silver particles, a combination of silver and ceramic particles, copper particles, glass-copper particles, a combination of copper and ceramic particles, a combination of copper and silver particles, and a combination of copper, silver and ceramic particles.

31. The electromyography needle of claim 30, wherein a plurality of the anti-microbial particles partially protrude through the top coating.

32. The electromyography needle of claim 29, wherein the sharpened tip portion has no coating.

33. An electromyography needle comprising:
an electrode including an elongated body having a sharpened tip portion and a non-tip portion; and a coating on the non-tip portion of the electrode, the coating having a base and a top coating, the coating including an epoxy, a fluoropolymer, and a polyethylene.

34. The electromyography needle of claim 33, wherein the coating includes anti-microbial particles selected from the group consisting of: silver particles, silver-oxide particles, glass-silver particles, a combination of silver and ceramic particles, copper particles, glass-copper particles, a combination of copper and ceramic particles, a combination of copper and silver particles, and a combination of copper, silver and ceramic particles.

35. The electromyography needle of claim 34, wherein the top coating includes a plurality of particles of a low-friction material.

36. The electromyography needle of claim 35, wherein a plurality of the anti-microbial particles partially protrude through the top coating.

37. The electromyography needle of claim 33, wherein the sharpened tip portion has no coating.

* * * * *